(12) United States Patent
Delgado et al.

(10) Patent No.: US 6,828,444 B2
(45) Date of Patent: Dec. 7, 2004

US006828444B2

(54) PROCESS FOR USE IN 11-OXA PROSTAGLANDIN SYNTHESIS

(75) Inventors: Pete Delgado, Fort Worth, TX (US); Raymond E. Conrow, Crowley, TX (US); William D. Dean, Arlington, TX (US); Michael S. Gaines, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/663,855

(22) Filed: Sep. 16, 2003

(65) Prior Publication Data

US 2004/0063968 A1 Apr. 1, 2004

Related U.S. Application Data

(63) Continuation of application No. 10/227,912, filed on Aug. 26, 2002, now Pat. No. 6,620,947, which is a continuation of application No. 09/860,772, filed on May 18, 2001, now Pat. No. 6,441,196.
(60) Provisional application No. 60/205,692, filed on May 19, 2000.

(51) Int. Cl.$^7$ ............................................. C07D 307/20
(52) U.S. Cl. ....................................................... 549/214
(58) Field of Search .......................................... 549/214

(56) References Cited

U.S. PATENT DOCUMENTS

4,133,817 A    1/1979   Lourens et al.
5,994,397 A    11/1999  Selliah et al.

OTHER PUBLICATIONS

Arndt et al., "Stereospecific Synthesis of Modified Prostaglandins Derived from Carbohydrates. Part 1.," *S. Afr. J. Chem.* 34(4):121–127 (Jun. 1981).

Caballero et al., "Synthesis and Diels–Alder Reactivity of simple 1–Phenoxy–1,3–Dienes," *Tetrahedron Letters* 37(38):6951–6954 (1996).

Duclos et al., "A Simple Conversion of Polyols into Anhydroalditols," *Synthesis* pp. 1087–1090 (Oct. 1994).

Hanessian et al., Total Synthesis of 11–Oxaprostaglandin $F_{2\alpha}$ and $F_{2\beta}$. *Carbohydrate Research* 141(2):221–238 XP000644751 (1985).

Lourens et al., The Novel Stereospecific Synthesis of 11–oxapros–taglandin $F_{2\alpha}$, *Tetrahedron Letters*, No. 43:3719–3722 Pergamon Press (1975).

Thiem et al., "Synthese von oxaprostaglandinen aus 1,4:3, 6–Dianhydro–D–sorbit," *Liebigs Ann. Chem.* 2151–2164 XP0006444761 (1985).

*Primary Examiner*—Taofiq Solola
(74) *Attorney, Agent, or Firm*—Barry L. Copeland

(57) ABSTRACT

Novel processes useful in the preparation of 11-oxa prostaglandin analogs are disclosed.

5 Claims, No Drawings

PROCESS FOR USE IN 11-OXA PROSTAGLANDIN SYNTHESIS

RELATED APPLICATION

The present application is a continuation application of U.S. patent application Ser. No. 10/227,912 filed Aug. 26, 2002 (now U.S. Pat. No. 6,620,947), which is a continuation of U.S. Ser. No. 09/860,772 filed May 18, 2001, now U.S. Pat. No. 6,441,196, which was based upon Provisional Application Ser. No. 60/205,692 filed May 19, 2000.

FIELD OF THE INVENTION

The present invention relates to novel compounds and processes useful in the synthesis of certain prostaglandin analogs. Specifically, the invention relates to intermediates and processes useful in the synthesis of certain 11-oxa prostaglandins.

BACKGROUND OF THE INVENTION

Substituted tetrahydrofuran analogs of D and F series prostaglandins for use in treating glaucoma and ocular hypertension are disclosed in commonly assigned U.S. Pat. No. 5,994,397, the entire contents of which are by this reference incorporated herein. 11-oxa $PGF_{2\alpha}$, analogs and/or synthetic schemes for their preparation are disclosed in Hanessian, et al., Carbohydrate Research, 141:221–238 (1985); Thiem et al., Liebigs Ann. Chem., 2151–2164 (1985); Arndt, et al., S. African J. Chem. 34:121–127 (1981); and U.S. Pat. No. 4,133,817. The entire contents of these references are hereby incorporated herein.

Previous routes to 11-oxa prostaglandins employ a C1–C2 olefination reaction of a tetrahydrofuran-2-carboxaldehyde for the introduction of the ω-chain. The α-chain may be introduced before or after this step. The tetrahydrofuran-2-carboxaldehyde may be prepared from several readily available carbohydrates, which provide the four carbons of the tetrahydrofuran core and C1 of the ω-chain. The following carbohydrates have been used as starting materials in this approach: D-sorbitol (J. Thiem and H. Luders, Liebigs Ann. Chem., 2151 (1985) and S. Hanessian, Y. Guindon, P. Lavallee and P. Dextraze, Carbohydrate Research, 141, 221 (1985)), D-xylose and D-glucose (G. J. Lourens and J. M. Koekemoer, Tetrahedron Letters, 43:3719 (1975) and R. R. Arndt, J. M. Koekemoer, G. J. Lourens and E. M. Venter, S.-Afri. Tydskr. Chem., 34:121 (1981)).

It is desirable, especially to improve therapeutic effect, to isolate the active isomer of the desired compound. In order for development of a pharmaceutical product comprising the enantiomerically enriched compound to be feasible, an economically viable synthetic route that will yield commercial quantities of the material is required.

Previously known syntheses of 11-oxa prostaglandins have suffered from various drawbacks that limit their usefulness for production of commercial quantities of the desired material. Such drawbacks include, without limitation, low yields, costly, time consuming, or inefficient synthetic sequences, and/or difficult or inadequate separation of the undesired enantiomer or epimer. A need exists, therefore, for an improved, commercially viable synthetic approach for. 11-oxa prostaglandin analogs.

SUMMARY OF THE INVENTION

The present invention is directed to novel processes and intermediates useful in the preparation of preferred enantiomers of certain 11-oxa prostaglandins. The processes and intermediates of the present invention are particularly useful in the preparation of [2R(1E,3R),3S(4Z),4R]-7-[Tetrahydro-2-[4-(3-chlorophenoxy)-3-hydroxy-1-butenyl]-4-hydroxy-3-furanyl]-4-heptenoic acid and its C1 esters.

DETAILED DESCRIPTION OF THE INVENTION

The present invention is directed to improved processes and intermediates for the preparation of certain 11-oxa prostaglandin analogs, including salt, ester, ether, alcohol, amine and amide derivatives thereof, and especially the 11-oxa prostaglandin analogs of formula I:

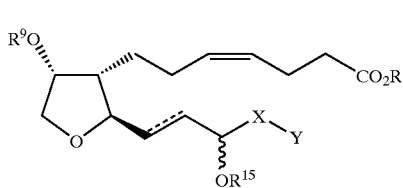

I wherein:

R is H or a pharmaceutically acceptable cationic salt moiety, or $CO_2R$ forms a pharmaceutically acceptable ester moiety;

$R^9O$ and $R^{15}O$ are the same or different and constitute a free or functionally modified hydroxy group;

===is a single or trans double bond;

$X=(CH_2)_q$ or $(CH_2)_qO$; q=1–6; and

Y=a phenyl ring optionally substituted with alkyl, halo, trihalomethyl, alkoxy, acyl, or a free or functionally modified hydroxy or amino group;

or $X-Y=(CH_2)_m Y^1$, m=0–6,

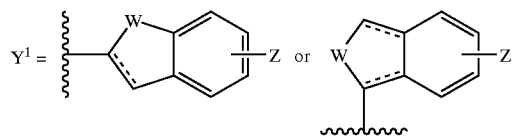

wherein:

$W=CH_2$, O, $S(O)_m$, $NR^{10}$, $CH_2CH_2$, $CH=CH$, $CH_2O$, $CH_2S(O)_m$, $CH=N$, or $CH_2NR^{10}$;

m=0–2;

$R^{10}$=H, alkyl, acyl;

Z=H, alkyl, alkoxy, acyl, acyloxy, halo, trihalomethyl, amino, alkylamino, acylamino, OH; and ====is a single or double bond.

The inventive processes and intermediates are preferably used to prepare the 11-oxa prostaglandin analogs of formula II:

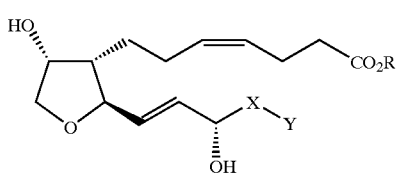

II wherein:

R=H or alkyl;

X=CH$_2$CH$_2$ or CH$_2$O; and
Y=phenyl, optionally substituted with halo or trihalomethyl.

The most preferred product of the presently claimed processes is isopropyl [2R(1E,3R),3S(4Z),4R]-7-[Tetrahydro-2-[4-(3-chlorophenoxy)-3-hydroxy-1-butenyl]-4-hydroxy-3-furanyl]-4-heptenoate as provided by formula II, wherein R=isopropyl, X=CH$_2$O, and Y=3-chlorophenyl.

It has now been discovered that by utilizing novel intermediates and by making certain modifications and additions to known synthetic processes, yields and purity of intermediates and ultimately the desired end product are significantly improved. The improved processes of the present invention thus provide a commercially viable route for the preparation of therapeutically useful 11-oxa prostaglandin analogs.

The novel process comprises conversion of D-sorbitol (1) to anhydro-D-glucitol (2) using acid and heat. Treatment of 2 with a trialkyl orthoalkanoate (preferred is trimethyl orthoacetate) affords ortho ester III (R$^3$ is alkyl or cycloalkyl, preferred is R$^3$=CH$_3$), which is silylated on the free hydroxy group using a silyl halide or triflate R$^4$R$^5$R$^6$SiX (R$^4$, R$^5$, R$^6$=same or different=alkyl, cycloalkyl, or aryl, preferred is R$^4$ and R$^5$=Ph and R$^6$=tert-butyl; X=Cl, Br, I, or OSO$_2$CF$_3$, preferred is X=Cl or OSO$_2$CF$_3$) in the presence of an amine base (e.g., NEt$_3$ or imidazole) to give silyl ether IV (R$^4$, R$^5$, R$^6$=same or different=alkyl, cycloalkyl, or aryl, preferred is R$^4$ and R$^5$=Ph and R$^6$=tert-butyl).

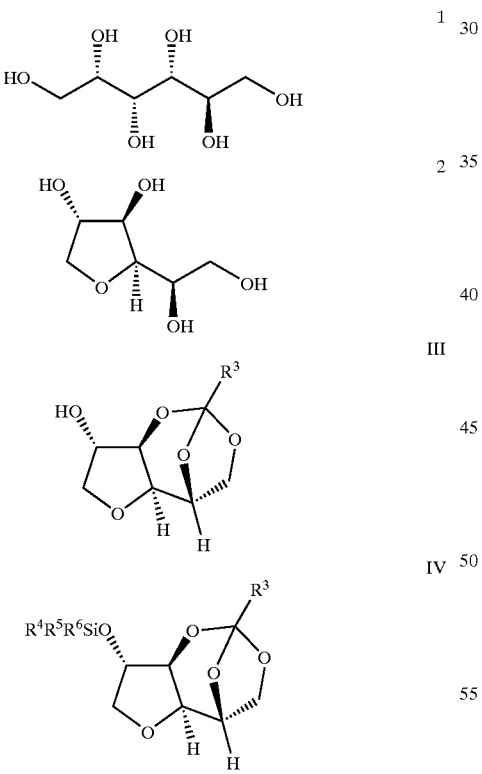

Treatment of IV with acid and a hydroxylic solvent provides triol V, which is treated with dimethoxypropane in the presence of catalytic acid to yield acetonide VI. Oxidation of VI with, for example, DMSO/carbodiimide/acid affords ketone VII, which is condensed with Ph$_3$P=CHCO$_2$R$^7$ (R$^7$=alkyl, aryl, or cycloalkyl; R$^7$=alkyl is preferred) to give enoate VIII (R$^7$=alkyl, aryl, or cycloalkyl, R$^7$=alkyl is preferred).

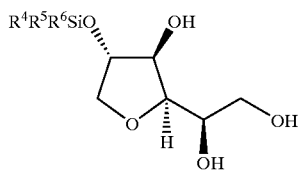

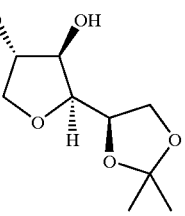

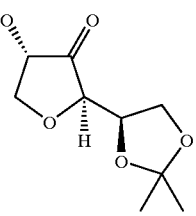

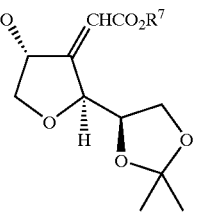

Unsaturated ester VIII is reduced with hydrogen gas over a metal catalyst (e.g., is Pd/C) to provide saturated ester IX, which is reduced with a metal hydride reagent (e.g., lithium aluminum hydride or lithium borohydride; preferred is lithium aluminum hydride) to give alcohol X. Treatment of alcohol X with R$^8$SO$_2$X (R$^8$=alkyl, aryl, or trifluoromethyl, preferred is methyl, 4-methylphenyl, or trifluoromethyl; X=halide, preferably chloride, or OSO$_2$R$^8$ (i.e., R$^8$SO$_2$X forms an anhydride)) in the presence of an amine base (such as pyridine, triethylamine, or DBU) yields sulfonate XI, which is reacted with a metal cyanide (preferably NaCN) in DMSO to afford nitrile XII. Oxidative deprotection of XII with H$_5$IO$_6$ gives aldehyde XIII, which is condensed with (MeO)$_2$P(O)CH$_2$C(O)—X-Y (X and Y are as defined for formula I; preferred is X=O and Y 3-chlorophenyl) in the presence of an amine base (preferred are triethylamine and DBU) and LiCl or LiBr to provide trans-enone XIV. Alternatively, aldehyde XIII can be condensed with Ph$_3$P=CHC(O)—X-Y (X and Y are as defined for formula I) to afford XIV.

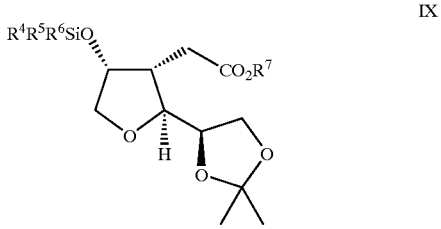

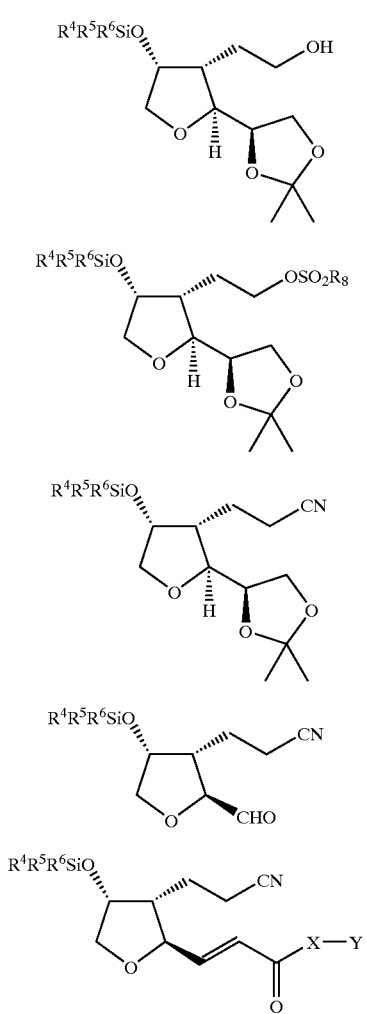

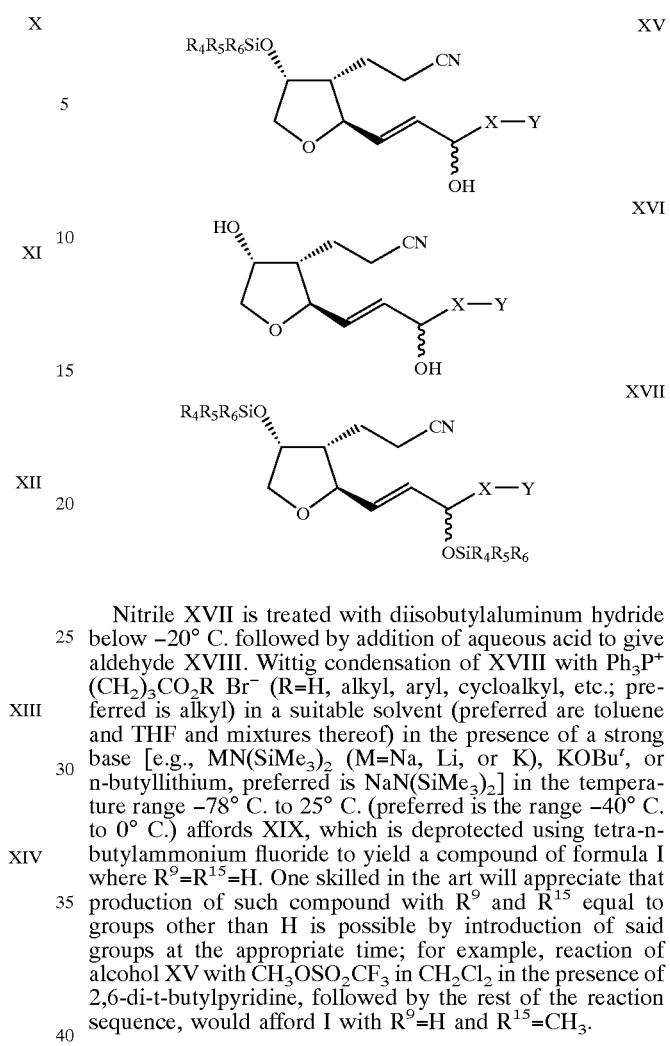

Reduction of enone XIV to the corresponding allylic alcohol can be performed under several conditions. Reduction using $NaBH_4CeCl_3$ affords the alcohol XV as a nearly 1:1 mixture of diastereomers. More efficient production of the 15α diastereomer can be achieved by using stoichiometric (−)-B-chlorodiisopinocampheylborane, or catalytic (3aR)-Tetrahydro-1-methyl-3,3-diphenyl-(1H,3H)-pyrrolo[1,2-c][1,3,2]oxazaborole [(R)-2-methyl-CBS-oxazaborolidine, which is commercially available from Aldrich Chemical Co., Milwaukee, Wis.] with stoichiometric $BH_3$ as the reducing agent. Similarly, use of stoichiometric (+)-B-chlorodiisopinocampheylborane, or catalytic (3aS)-Tetrahydro-1-methyl-3,3-diphenyl-(1H,3H)-pyrrolo[1,2-c][1, 3,2]oxazaborole [(S)-2-methyl-CBS-oxazaborolidine, which is commercially available from Aldrich Chemical Co., Milwaukee, Wis.] with stoichiometric $BH_3$ affords the 15β diastereomer predominantly. Optionally, desilylation of XV using tetra-n-butylammonium fluoride affords diol XVI, for which the normal phase silica gel chromatographic separation of the two carbon 15 epimers is most efficiently achieved. Protection of XV or XVI using a silyl halide or triflate $R^4R^5R^6SiX$ ($R^4$, $R^5$, $R^6$=same or different=alkyl, cycloalkyl, or aryl, preferred is $R^4$ and $R^5$ Ph and $R^6$=tert-butyl; X=Cl, Br, I, or $OSO_2CF_3$, preferred is X=Cl or $OSO_2CF_3$) in the presence of an amine base (e.g., $NEt_3$ or imidazole) provides XVII.

Nitrile XVII is treated with diisobutylaluminum hydride below −20° C. followed by addition of aqueous acid to give aldehyde XVIII. Wittig condensation of XVIII with $Ph_3P^+$ $(CH_2)_3CO_2R$ $Br^−$ (R=H, alkyl, aryl, cycloalkyl, etc.; preferred is alkyl) in a suitable solvent (preferred are toluene and THF and mixtures thereof) in the presence of a strong base [e.g., $MN(SiMe_3)_2$ (M=Na, Li, or K), $KOBu^t$, or n-butyllithium, preferred is $NaN(SiMe_3)_2$] in the temperature range −78° C. to 25° C. (preferred is the range −40° C. to 0° C.) affords XIX, which is deprotected using tetra-n-butylammonium fluoride to yield a compound of formula I where $R^9$=$R^{15}$=H. One skilled in the art will appreciate that production of such compound with $R^9$ and $R^{15}$ equal to groups other than H is possible by introduction of said groups at the appropriate time; for example, reaction of alcohol XV with $CH_3OSO_2CF_3$ in $CH_2Cl_2$ in the presence of 2,6-di-t-butylpyridine, followed by the rest of the reaction sequence, would afford I with $R^9$=H and $R^{15}$=$CH_3$.

The term "acyl" represents a group that is linked by a carbon atom that has a double bond to an oxygen atom and single bond to another carbon atom.

The term "acylamino" represents a group that is linked by an amino atom that is connected to a carbon atom that has a double bond to an oxygen group and a single bond to a carbon atom or hydrogen atom.

The term "acyloxy" represents a group that is linked by an oxygen atom that is connected to a carbon atom that has a double bond to an oxygen atom and single bond to another carbon atom.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkenyl groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched chain alkyl groups include methyl, ethyl, propyl, isopropyl, butyl and t-butyl.

The term "alkylamino" represents an alkyl group attached through a nitrogen linkage.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "cationic salt moiety" includes alkali and alkaline earth metal salts as well as ammonium salts.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "halogen" and "halo" represents fluoro, chloro, bromo, or iodo.

The term "lower alkyl" represents alkyl groups containing one to six carbons (C1–C6).

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-, heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, NHOH, and $NH(OCH_3)$.

For purposes of the foregoing and following definitions, the term "alkyl" or "pharmaceutically acceptable ester moiety" means any ester moiety that would be suitable for therapeutic administration to a patient by any conventional means without significant deleterious health consequences. Similarly, the term "ophthalmically acceptable ester moiety" means any pharmaceutically acceptable ester moiety that would be suitable for ophthalmic application, i.e. non-toxic and non-irritating. Preferred are ophthalmically acceptable esters such as alkyl and alkylcycloalkyl esters of carboxylic acids. Most preferred are C2–C5 alkyl esters of carboxylic acids, and especially isopropyl esters.

In the foregoing illustrations, as well as those provided hereinafter, wavy line attachments indicate that the configuration may be either alpha (α) or beta (β). Dashed lines on bonds indicate a single or double bond. Two solid lines between carbons specify the configuration of the relevant double bond. Hatched lines indicate the α configuration. A solid triangular line indicates the β configuration.

In the following Examples, the following standard abbreviations are used: g=grams (kg=kilograms; mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

The preparations exemplified below are depicted schematically in the following Scheme I. All reactions were performed under a nitrogen atmosphere.

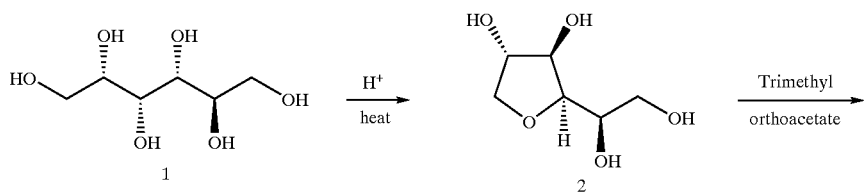

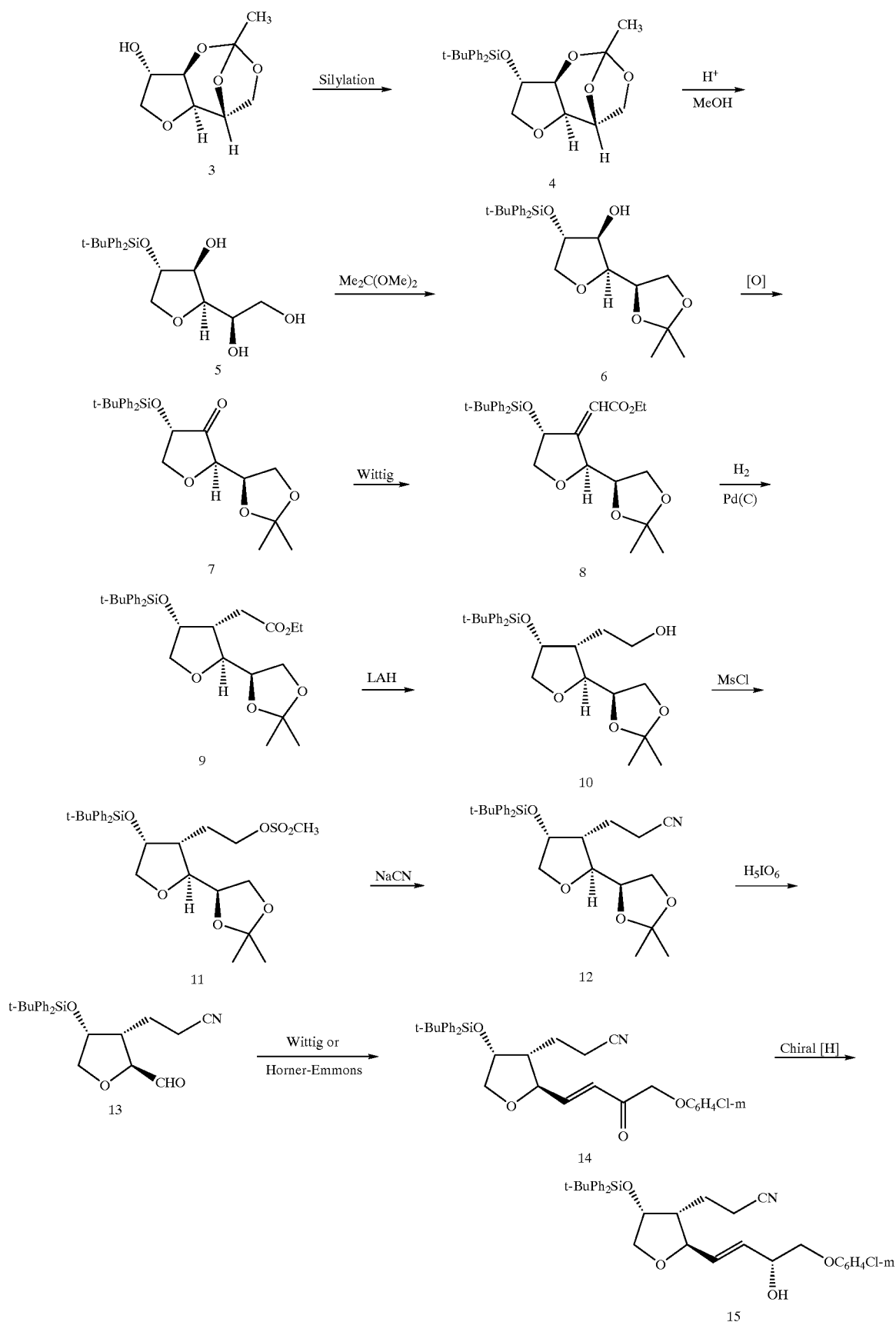

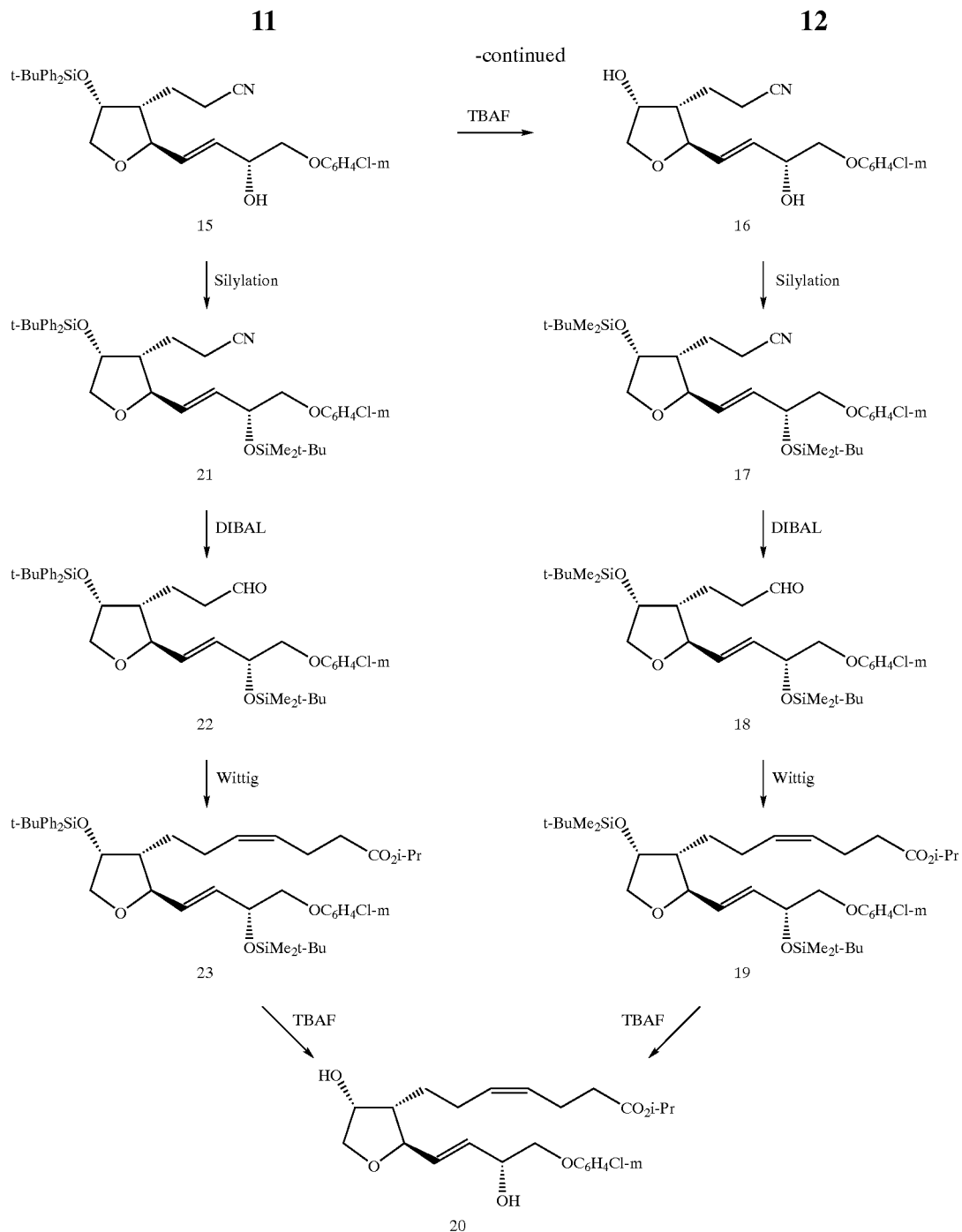

Preparation of 1,4-Anhydro-D-glucitol (1,4-anhydro-D-sorbitol) (2). A mixture of D-sorbitol (1) (4.0 kg), water (560 mL) and H$_2$SO$_4$ (50 mL) was heated to a melt (104° C.) and stirred. After 20 h, 25 mL of H$_2$SO$_4$ was added. After a farther 22 h, 25 mL of H$_2$SO$_4$ was added. After a further 32 h, the mixture was cooled to ambient temperature, neutralized carefully with solid Na$_2$CO$_3$ and stirred for 30 min. i-PrOH (12 L) was added, followed by anhydrous Na$_2$SO$_4$ (4 kg). The mixture was filtered and the solid was washed with i-PrOH (6 L) and EtOH (3 L). The filtrate was treated with activated charcoal (100 g), filtered through Celite, rinsing with 1.2 L each of i-PrOH and EtOH, then concentrated. Toluene (6 L) was added to the residue, and the mixture was concentrated in vacuo with heating to effect azeotropic removal of water. EtOH (10 L) was added to the solid residue with heating to effect dissolution. The solution was concentrated and cooled to ambient temperature to give a suspension (6 L). The solid was isolated by filtration, washed with cold EtOH (4 L) and dried. Recrystallization of the crude product (1.9 kg) from hot EtOH provided 2 (1693 g) as a white solid, mp 112–112.5° C., $[\alpha]^{23}_D$ –22.9°(c 0.5, H$_2$O). The $^{13}$C NMR spectrum of this compound agreed with that reported by Duclos et al., Synthesis, page 1087 (1994).

Preparation of 1,4-Anhydro-3,5,6-O-orthoacetyl-D-glucitol (3). Trimethyl orthoacetate (1513 mL) and p-TsOH.H$_2$O (15 g) were added to a stirred solution of 2 (1.5 kg) in MeCN (15 L). After 13 h, Na$_2$CO$_3$ (50 g) was added. After 15 min the mixture was filtered through Celite and the filtrate concentrated to give 3 (1760 g). The $^1$H and $^{13}$C NMR spectra of this compound agreed with those reported by Duclos et al., Synthesis, page 1087 (1994).

Preparation of 1,4-Anhydro-2-O-t-butyldiphenylsilyl-3,5,6-O-orthoacetyl-D-glucitol (4). t-BuPh$_2$SiCl (2495 mL) was added to a stirred solution of 3 (1720 g) and imidazole (1555 g) in DMF (3.0 L). After 19 h the mixture was poured into brine and extracted with 2:1 ether-hexane (4×6 L). The organic extract was washed with brine, dried (Na$_2$SO$_4$), filtered and concentrated to give 4 (4115 g) as a viscous oil. $^1$H NMR (CDCl$_3$): δ 1.06 (s,9H), 1.52 (s, 3H), 3.77–4.06 (m, 5H), 4.27 (br s, 2H), 4.74 (m, 1H), 7.34–748 (m, 6H), 7.60–7.64 (m, 4H).

Preparation of 1,4-Anhydro-2-O-t-butyldiphenylsilyl-D-glucitol (5). Amberlyst-15 resin (1 kg) and water (20 mL) were added to a stirred solution of 4 (1947 g) in MeOH (35 L). After 19 h the mixture was treated with activated charcoal (50 g) and filtered through Celite, rinsing with MeOH (6 L). The filtrate was combined with that from an identical run and concentrated in vacuo to give 5 (3948 g) as a solid. $^1$H NMR (CDCl$_3$): δ 1.05 (s, 9H), 3.05 (br s, 1H), 3.77–4.22 (m, 10H), 7.31–7.46 (m, 6H), 7.57–7.70 (m, 4H).

Preparation of 1,4-Anhydro-2-O-t-butyldiphenylsilyl-5,6-O-isopropylidene-D-glucitol (6). 2,2-Dimethoxypropane (842 mL) and p-TsOH.H$_2$O (3.4 g) were added to a stirred solution of 5 (918 g) in acetone (41 L) at 0° C. After 2 h the solution was eluted through Florisil (1 kg) and the filtrate was combined with those from three identical runs and concentrated. The solid residue was treated with hexane (12 L) and the resulting suspension was concentrated to 8 L. Crystalline 6 (2817 g) was obtained by filtration and drying in vacuo at 40° C. The $^1$H NMR spectrum of this compound agreed with that reported by Hanessian et al., Carbohydrate Research, Volume 141, page 221 (1985).

Preparation of 1,4-Anhydro-2-O-t-butyldiphenylsilyl-5,6-O-isopropylidene-D-ribo-3-hexulose (7). Dichloroacetic acid (263 mL) was added over 15 min to a stirred mixture of 6 (2815 g) and 1-(3-(dimethylamino)propyl)-3-ethylcarbodiimide hydrochloride (3663 g) in DMSO (25 L). After 4 h the mixture was poured into 5% NaHCO$_3$ (37 L) and extracted with 1:1 ether-hexane (4×12 L). The organic extract was washed with water (9 L), brine (9 L), dried over a mixture of MgSO$_4$ and activated carbon, filtered and concentrated. The residue was dissolved in ether (1 L) and eluted through silica gel with ether (12 L). Concentration in vacuo gave 7 (2783 g) as a yellow oil. The $^1$H NMR spectrum of this compound agreed with that reported by Hanessian et al., Carbohydrate Research, Volume 141, page 221 (1985).

Preparation of 1,4-Anhydro-2-(t-butyldiphenysilyl)oxy-3-deoxy-3-C-(ethoxycarbonylmethylene)-5,6-O-isopropylidene-D-ribo-hexitol (8). Ph$_3$P=CHCO$_2$Et (3.5 kg) was added to a stirred solution of 7 (2782 g) in CH$_2$Cl$_2$ (25 L). After 48 h the mixture was applied to a silica gel pad and eluted with 20% EtOAc-hexane. Concentration in vacuo gave 8 (3337 g). The $^1$H NMR spectrum of this compound agreed with that reported by Hanessian et al., Carbohydrate Research, Volume 141, page 221 (1985).

Preparation of 1,4-Anhydro-2-(t-butyldiphenysilyl)oxy-3-deoxy-3-C-(ethoxycarbonylmethyl)-5,6-O-isopropylidene-D-allitol (9). A solution of 8 (1622 g) in EtOH (2.6 L) was added to a suspension of Raney Ni (2 kg, washed with 3×3 L of water) in EtOH (4 L). After stirring for 30 min, the mixture was filtered through Celite, rinsing with hot EtOH (12 L). The filtrate was charged into a 20-L steel reactor. Pd on carbon (10%, 50 g) was added as a suspension in EtOH-water, and the reactor was then purged with H$_2$. The mixture was stirred at ambient temperature under 1.5–2 atm of H$_2$ pressure for 24 h. Pd on carbon (10%, 100 g) was added and the hydrogenation was resumed under the foregoing conditions until complete by NMR analysis. The mixture plus reactor rinse (4 L of EtOH) was filtered through Celite, rinsing with additional EtOH. Toluene was added to the filtrate and the solution was concentrated in vacuo to give 9 (1602 g). The $^1$H NMR spectrum of this compound agreed with that reported by Hanessian et al., Carbohydrate Research, Volume 141, page 221 (1985).

Preparation of 1,4-Anhydro-2-(t-butyldiphenysilyl)oxy-3-deoxy-3-C-(2-hydroxyethyl)-5,6-O-isopropylidene-D-allitol (10). LiAlH$_4$ (1 M in THF, 2.4 L) was added over 40 min to a stirred, ice-cooled solution of 9 (1602 g) in ether (24 L), keeping the reaction temperature below 5° C. After stirring for a further 2 h with ice cooling, the reaction was carefully quenched by sequential addition of water (91 mL), 15% NaOH (91 mL), and water (273 mL) The mixture was stirred until the solid separated in granular form, then filtered through Celite. The filter cake was rinsed with hot EtOAc (30 L), the filtrate was concentrated and the residue was eluted through a silica gel pad with 25% EtOAc-hexane followed by EtOAc. Concentration in vacuo gave 10 (1229 g) as an oil. $^1$H NMR (CDCl$_3$): δ 1.07 (s, 9H), 1.34 (s, 3H), 1.43 (s,3H), 1.79–1.86 (m, 1H), 202–2.16 (m, 2H), 3.45–4.39 (m, 9H), 7.33–7.45 (m, 6H), 7.62–7.69 (m, 4H).

Preparation of 1,4-Anhydro-2-(t-butyldiphenysilyl)oxy-3-deoxy-3-C-(2-(mesyloxy)ethyl)-5,6-O-isopropylidene-D-allitol (11). MsCl (202 mL) was added to a stirred, ice-cooled solution of 10 (1226 g) and Et$_3$N (726 mL) in CH$_2$Cl$_2$ (12 L), keeping the reaction temperature below 10° C. After stirring for a further 1 h with ice cooling, the mixture was quenched into water (6 L) and the organic solution was separated. The aqueous solution was extracted with CH$_2$Cl$_2$ (3×4 L) and the combined organic extract was washed with saturated KH$_2$PO$_4$ (3×2 L) and brine (2 L), dried (Na2SO$_4$) and concentrated to provide 11 (1445 g) as an oil. $^1$H NMR (CDCl$_3$): δ 1.07 (s, 9H), 1.33 (s, 3H), 1.42 (s, 3H), 2.00–2.25 (m, 2H), 2.92 (s, 3H), 3.53–4.37 (m, 7H), 7.36–7.36–7.49 (m, 6H), 7.62–7.68 (m, 4H).

Preparation of 1,4-Anhydro-2-(t-butyldiphenysilyl)oxy-3-deoxy-3-C-(2-cyanoethyl)-5,6-O-isopropylidene-D-allitol (12). NaCN (166 g) was added to a stirred solution of 11 (1445 g) in DMSO (8 L) at 35° C. After 24 b, NaCN (38 g) was added and the temperature was raised to 45° C. After a further 24 h, the mixture was cooled to ambient temperature and poured into water (30 L) containing 5 kg of ice. NaCl (5 kg) was added and the mixture was extracted with ether (4×8 L). The organic extract was washed with brine (15 L), dried (Na$_2$SO$_4$) and concentrated. The residue (1.2 kg) was dissolved in 5% EtOAc-hexane (4 L) and this solution was injected into a Biotage Kiloprep 250 chromatographic instrument (run 1, 400 g; run 2, 800 g) eluting with 5% EtOAc-hexane, then 20% EtOAc-hexane, and finally EtOAc, to provide 12 (1025 g) as a clear oil. $^1$H NMR (CDCl$_3$): δ 1.08 (s, 9H), 1.33 (s, 3H), 1.42 (s, 3H), 1.96–2.28 (m, 5H), 3.52–3.58 (dd, 1H), 3.67–3.79 (m, 2H), 3.88–3.93 (m, 2H), 4.05–4.10 (m, 1H), 4.32 (s, 1H), 7.34–7.47 (m, 6H), 7.61–7.67 (m, 4H).

Preparation of (2S, 3R, 4R)-4-(t-Butyldipbenylsilyl)oxy-3-(2-cyanoethyl)tetrahydrofuran-2-carboxaldehyde (13). H$_5$IO$_6$ (625 g) was added to a stirred solution of 12 (1024 g) in ether (20 L). After 18 h the mixture was applied to a 25-cm pad of Florisil and eluted with 1:1 EtOAc-hexane. Concentration in vacuo gave 13 (870 g) largely as the hydrate. $^1$H NMR (CDCl$_3$): δ 1.08 (s, 9H), 2.08–2.25 (m, 5H), 3.69–3.76 (dd, 1H), 3.89–3.94 (d, 1H), 4.13–4.19 (m, 1H), 4.38 (t, 1H), 7.37–7.48 (m, 6H), 7.62–7.68 (m, 4H), 9.69 (d, 35% of 1H).

Preparation of (2R (1E), 3R, 4R)-3-[Tetrahydro-(2-(4-(3-chlorophenoxy)-3-oxo-1-butenyl)-4-(t-butyldiphenylsilyl)oxy)-3-furanyl]propanenitrile (14).

Method 1. N,N-Diisopropylethylamine (408 mL) was added dropwise to a stirred solution of 13 (870 g), dimethyl 3-(3-chlorophenoxy)-2-oxopropyl phosphonate (640 g) and LiCl (102 g) in MeCN (10 L). After complete reaction, hexane-ether (1:4, 40 L) was added and the solution was washed with saturated $KH_2PO_4$ (2×4 L) and brine (2×4 L), dried ($Na_2SO_4$) filtered and concentrated. The residue was chromatographed on a Biotage Kiloprep 250, eluting with a step gradient of 5% to 15% EtOAc-hexane to give 14 (173 g) of 75% purity. $^1$H NMR ($CDCl_3$): δ 1.09 (s, 9H), 1.64–1.87 (m, 2H), 2.05–2.15 (m, 2H), 3.70–3.77 (dd, 1H), 3.85–3.90 (d, 1H), 4.36 (t, 1H), 4.43–4.50 (m, 1H), 4.71 (s, 2H), 6.60–6.69 (d, 1H), 673–6.80 (dd, 1H), 6.88–7.00 (m, 3H), 7.16–7.24 (t, 1H), 7.35–7.48 (m, 6H), 7.61–7.68 (m, 4H).

Method 2. The procedure of Tome et al., Tetrahedron Letters, Volume 37, pp 6951–6954 (1996), was followed. 1,3-Dichloroacetone (8.0 g) and $Ph_3P$ (15.0 g) were stirred in THF (38 mL) at reflux for 4 h. The cooled suspension was diluted with ether, filtered and the solid was washed with ether and dried to give (3-chloro-2-oxopropyl)triphenylphosphonium chloride (20.86 g) as a white solid. This material was dissolved in a mixture of water (110 mL) and MeOH (110 mL) and treated with $NaHCO_3$ (10.3 g). The resulting white precipitate was collected by filtration, washed with water and dried in vacuo to give 1-chloro-3-(triphenylphosphanylidene)-2-propanone (18.25 g). A solution of this phosphorane (18.2 g) and 3-chlorophenol (7.28 g) was stirred with $K_2CO_3$ (28.57 g) in DMSO (91 mL) at 62° C. for 18 h, then diluted with water (2 L), extracted with ether (3×1 L), dried ($MgSO_4$), filtered and concentrated to give 1-(3-chlorophenoxy)-3-(triphenylphosphanylidene)-2-propanone (21.7 g) as a tan solid. $^1$H NMR ($CDCl_3$): δ 4.02 (s, 2H), 4.23–4.35 (d, 1H), 7.42–7.72 (m, 15H).

$H_5IO_6$ (3.15 g) was added to a stirred solution of 12 (5.3 g) in ether (100 mL). After 18 h, the mixture was eluted through Celite with ether and concentrated. The residue was dissolved in $CH_2Cl_2$ (53 mL). Molecular sieves (4A, 0.75 g) and 1-(3-chlorophenoxy)-3-(triphenylphosphanylidene)-2-propanone (7.81 g) were added, and the mixture was stirred for 18 h., then eluted through Florisil with 10% EtOAc-hexane. The crude product obtained upon concentration was chromatographed on silica gel, eluting with 18% EtOAc-hexane, to give 14 (5.77 g) as a colorless oil.

Preparation of (2R (1E), 3R), 3R, 4R)-3-[Tetrahydro-(2-(4-(3-chlorophenoxy)-3-hydroxy-1-butenyl)-4-(t-butyldiphenylsilyl)oxy)-3-furanyl]propanenitrile (15). A solution of 14 (172 g) in anhydrous THF (1.2 L) was added at 10° C. to a stirred solution of (R)-2-methyl-CBS-oxazaborolidine (1 M in toluene, 30 mL), BH3.THF (1 M in THF, 179 mL) and anhydrous THF (100 mL), keeping the reaction temperature at 10° C. After complete reaction, MeOH (300 mL) was carefully added and the solution was concentrated. The residue (180 g) was chromatographed on a Biotage Kiloprep 250 eluting with 30% EtOAc-hexane to give 90 g of material which was rechromatographed eluting with 6% i-PrOH-hexane to give 15 (68 g) containing 6% of the 15-epimer and 9% of an unknown impurity. $^1$H NMR ($CDCl_3$): δ 1.09 (s, 9H), 1.70–1.75 (m, 1H), 1.81–1.86 (m, 1H), 2.03–2.26 (m, 3H), 2.40 (s, 1H), 3.78–3.81 (dd, 1H), 3.85–3.87 (d, 1H), 3.92–3.96 (m, 1H), 4.02–4.05 (dd, 1H), 4.33–4.36 (m, 1H), 4.40 (t, 1H), 4.92 (m, 1H), 5.90–5.97 (m, 2H), 6.83–6.87 (m, 1H), 6.95–7.01 (m, 2H), 7.25 (t, 1H), 7.42–7.68 (m, 6H), 7.66–7.72 (m, 4H).

Preparation of (2R (1E), 3R), 3R, 4R)-3-[Tetrahydro-(2-(4-(3-chlorophenoxy)-3 -hydroxy-1-butenyl)-4-hydroxy)-3-furanyl]propanenitrile (16). Neat 15 (26 g, 0.045 mol) was treated with tetrabutylammonium fluoride (1M in THF, 225 mL). The solution was stirred for 1.5 h, then quenched with water (1 L) and extracted with EtOAc (4×600 mL). The organic extract was washed with brine (500 mL), dried ($MgSO_4$), filtered and concentrated. The residue was chromatographed on a Biotage Kiloprep 250 instrument with 20% acetone-$CH_2Cl_2$. Fractions containing <1% of the 15-epimer by HPLC were combined and concentrated in vacuo to afford 16 (8.8 g) containing 0.9% of the 15-epimer. $^1$H NMR ($CDCl_3$): δ 1.66–1.73 (m, 1H), 1.87–2.03 (m, 2H), 2.47 (t, 2H), 3.83–3.92 (m, 2H), 3.98–4.01 (dd, 1H), 4.11–4.16 (m, 2H), 4.45 (t, 1H), 4.55–4.57 (m, 1H), 5.86 (br s, 2H), 6.80–6.81 (d, 1H), 6.91–6.96 (m, 2H), 7.20 (t, 1H).

Preparation of (2R (1E), 3R), 3R, 4R)-3-[Tetrahydro-(2-(4-(3-chlorophenoxy)-3-(t-butyldimethylsilyl)oxy-1-butenyl)-4-(t-butyldimethylsilyl)oxy)-3-furanyl]propanenitrile (17). t-$BuMe_2SiCl$ (19.6 g) was added to a stirred solution of 16 (8.8 g) and imidazole (18.2 g) in DMF (100 mL). After 18 h, water (400 mL) was added and the mixture was extracted with ether (3×500 mL). The organic extract was washed with brine (500 mL), dried ($MgSO_4$), filtered and concentrated. The residue was chromatographed on silica gel (hexane to 20% EtOAc-hexane) to afford 17 (11.6 g). $^1$NMR ($CDCl_3$): δ 0.10 (s, 12H), 0.91 (s, 18H), 1.45–1.70 (m, 1H), 1.73–2.01 (m, 2H), 2.32–2.43 (m, 2H), 3.71–3.77 (dd, 1H), 3.83–3.87 (d, 2H), 4.04–4.14 (m, 2H), 4.38 (t, 1H), 4.49–4.57 (m, 1H), 5.79–5.84 (m, 2H), 6.74–6.79 (ddd, 1H), 6.86–6.95 (m, 2H), 7.18 (t, 1H).

Preparation of (2R (1E), 3R), 3R, 4R)-3-[Tetrahydro-(2-(4-(3-chlorophenoxy)-3-(t-butyldimethylsilyl)oxy-1-butenyl)-4-(t-butyldimethylsilyl)oxy)-3-furanyl]propanal (18). Diisobutylaluminum hydride (1 M in toluene, 131 mL) was added dropwise to a stirred solution of solution of 17 (11.6 g) in toluene (230 mL), keeping the reaction temperature below −65° C. After 2.5 h, 5% HOAc in water (270 mL) was added and the mixture (pH 4) was allowed to warm to 0° C., then extracted with ether (3×500 mL). The organic extract was washed with water to pH 6, then with 2% $NaHCO_3$ (500 mL), dried ($Na_2SO_4$), filtered and concentrated. The residue was chromatographed at once on silica gel (hexane to 10% EtOAc-hexane) giving 18 (10.3 g) as a clear oil. $^1$H NMR ($CDCl_3$): δ 0.11–0.13 (d, 12H), 0.83 (s, 18H), 1.50–1.89 (m, 3H), 2.33–2.44 (m, 2H), 3.65–3.69 (d, 1H), 3.76–3.79 (d, 2H), 3.93–4.08 (m, 2H), 4.25 (t, 1H), 4.42–4.49 (m, 1H), 5.71–5.75 (m, 2H), 6.66–6.71 (m, 2H), 7.15 (t, 1H), 9.64 (s, 1H).

Preparation of Isopropyl [2R (1E, 3R), 3R (4Z), 4R]-7-[tetrahydro-(2-(4-(3-chlorophenoxy)-3-(t-butyldimethylsilyl)oxy-1-butenyl)-4-(t-butyldimethylsilyl)oxy)-3-furanyl]-4-heptenoate (19).

A solution of 4-bromobutyric acid (50 g) in 2-propanol (200 mL) containing 1 mL of $H_2SO_4$ was refluxed for 3 h, then cooled to ambient temperature, diluted with ether (500 mL), washed with saturated $NaHCO_3$ (3×300 mL), and brine (300 mL). The organic extract was dried ($MgSO_4$), filtered and concentrated in vacuo to give isopropyl 4-bromo-butyrate (52 g) as an oil. This ester was dissolved in MeCN (380 mL). $Ph_3P$ (100 g) was added and the solution was heated at reflux for 72 h, after which TLC analysis (20% water/MeCN, C-18 RP TLC plates) showed complete reaction. The mixture was cooled and concentrated and the residue was slurried with toluene (400 mL) for 1 h. The solid was collected by filtration and was washed with toluene (100 mL) and then dried in vacuo at 50° C. to provide (3-(isopropoxycarbonyl)propyl)triphenylphosphonium bromide (100.6 g). $^1$H NMR (CDCl$_3$): δ 1.19–1.22 (d, 6H), 1.85–1.97 (m, 2H), 2.85 (t, 2H), 3.95–4.10 (m, 2H), 4.89–5.03 (m, 1H), 7.65–7.94 (m, 15H).

NaN(SiMe$_3$)$_2$ (1 M in THF, 36 mL) was added dropwise to a stirred suspension of (3-(isopropoxycarbonyl)propyl)triphenylphosphonium bromide (17.0 g) in THF (95 mL) at −37° C. After 20 min, a solution of 18 (10.3 g) in toluene (95 mL) was added dropwise over 30 min, keeping the reaction temperature below −10° C. After 10 min the reaction was quenched with i-PrOH (40 mL), allowed to warm to ambient temperature and then treated with saturated KH$_2$PO4 (750 mL). After stirring for 10 min, the mixture was separated and the aqueous solution was extracted with ether (2×600 mL). The combined organic extract was dried (Na$_2$SO$_4$), filtered and concentrated. The residue was chromatographed on silica gel eluting with a step gradient of hexane to 30% EtOAc-hexane, to give 19 (9.5 g) as a clear oil. $^1$H NMR (CDCl$_3$): δ 0.08 (s, 12H), 0.90 (br s, 18H), 1.21–1.24 (d, 6H), 1.22–1.27 (m, 1H), 1.62–1.68 (m, 2H), 2.07–2.10 (m, 2H), 2.29–2.34 (m, 4H), 3.73–3.75 (d, 1H), 3.83–3.85 (m, 2H), 3.99–4.02 (dd, 1H), 4.03–4.08 (m, 1H), 4.38 (t, 1H), 4.50–4.53 (q, 1H), 4.96–5.03 (m, 1H), 5.32–5.43 (m, 2H), 5.77–5.80 (m, 2H), 6.73–6.76 (dd, 1H), 6.86 (s, 1H), 6.89–6.91 (d, 1H), 7.16 (t, 1H).

Preparation of (2R (1E, 3R), 3R, 4R)-3-[Tetrahydro-(2-(4-(3-chlorophenoxy)-3-(t-butyldimethylsilyl)oxy-1-butenyl)-4-(t-butyldiphenylsilyl)oxy)-3-furanyl]propanenitrile (21).
t-BuMe$_2$SiCl (34.7 g) was added to a stirred solution of 15 (66 g) and imidazole (32.2 g) in DMF (760 mL). After 2.5 h the reaction was quenched with water (4 L) and extracted with ether (3×3 L). The organic extract was washed with brine, dried (Na$_2$SO$_4$), filtered and concentrated. The residue was chromatographed on silica gel eluting with EtOAc-hexane to give bis silyl ether 21 (72 g) as an oil. $^1$H NMR (CDCl$_3$): δ 0.09 (s, 6H), 0.90 (s, 9H), 1.09 (s, 9H), 1.58–1.66 (m, 1H), 1.72–1.76 (m, 1H), 1.97–2.16 (m, 3H), 3.75–3.85 (m, 4H), 4.27 (t, 1H), 4.36 (t, 1H), 4.51–454 (q, 1H), 5.75–5.89 (m, 2H), 6.75–6.77 (dd, 1H), 6.87 (s, 1H), 6.91–6.93 (d, 1H), 7.18 (t, 1H), 7.38–7.49 (m, 6H), 7.62–7.65 (m, 4H).

Preparation of (2R (1E, 3R), 3R, 4R)-3-[Tetrahydro-(2-(4-(3-chlorophenoxy)-3-(t-butyldimethylsilyl)oxy-1-butenyl)-4-(t-butyldiphenylsilyl)oxy)-3-furanyl]propanal (22). Diisobutylaluminum hydride (1 M in toluene, 191 mL) was added to a stirred solution of 21 (72 g) in toluene (1420 mL) keeping the reaction temperature below −65° C. After 2.5 h, 5% HOAc in water (1.4 L) was added and the mixture (pH 4) was allowed to warm to 0° C., then extracted with ether (8 L). The organic extract was washed with water and brine (to pH 6), dried (Na$_2$SO$_4$), filtered and concentrated. The residue was chromatographed at once on silica gel (hexane to 10% EtOAc-hexane) giving 22 (63.2 g) as a clear oil. $^1$H NMR (CDCl$_3$): δ 0.07 (s, 6H), 0.88 (s, 9H), 1.08 (s, 9H), 1.53–1.68 (m, 1H), 1.84–1.99 (m, 1H), 2.22 (t, 2H), 3.71–3.73 (dd, 1H), 3.77–3.92 (d, 1H), 3.83–3.85 (d, 2H), 4.28 (t, 1H), 4.33 (t, 1H), 4.51–4.54 (q, 1H), 5.74–5.88 (m, 2H), 6.74–6.77 (dd, 1H), 6.86 (s, 1H), 6.90–6.91 (d, 1H), 7.17 (t, 1H), 7.37–7.44 (m, 6H), 7.63–7.66 (m, 4H), 9.58 (s, 1H).

Preparation of Isopropyl [2R (1E, 3R), 3R (4Z), 4R]-7-[tetrahydro-(2-(4-(3-chlorophenoxy)-3-(t-butyldimethylsilyl)oxy-1-butenyl]-4-(t-butyldiphenylsilyl)oxy)-3-furanyl]-4-heptenoate (23). NaN(SiMe$_3$)2 (1 M in THF, 181 mL) was added dropwise to a stirred suspension of (3-(isopropoxycarbonyl)propyl)triphenylphosphonium bromide (85 g) in THF (620 mL) at −37° C. After 20 min, a solution of 22 (62.5 g) in toluene (620 mL) was added dropwise over 30 min while maintaining the reaction temperature below −10° C. After 10 min the reaction was quenched with i-PrOH (192 mL), allowed to warm to ambient temperature and then treated with saturated KH$_2$PO$_4$ (3.6 L). After stirring for 10 min, the mixture was separated and the aqueous solution was extracted with ether (2×4 L). The combined organic extract was dried (Na$_2$SO$_4$), filtered and concentrated. The residue was chromatographed on silica gel eluting with a step gradient of hexane to 30% EtOAc-hexane, to give 23 (61.5 g) as a clear oil. $^1$H NMR (CDCl$_3$): δ 0.07 (s, 6H), 0.89 (s, 9H), 1.08 (s, 9H), 1.21–1.26 (d, 6H), 1.24–1.29 (m, 1H), 1.57–1.61 (m, 1H), 1.78 –1.88 (s, 1H), 1.92–1.99 (m, 2H), 2.21–2.27 (m, 4H), 3.62–3.64 (d, 1H), 3.73–3.75 (d, 1H), 3.83–3.84 (d, 2H), 4.25–4.30 (t, 1H), 4.34 (t, 1H), 4.49–4.51 (m, 1H), 4.96–5.03 (m, 1H), 5.28–5.31 (m, 2H), 5.72–5.84 (m, 2H), 6.75–6.78 (d, 1H), 6.86 (s, 1H), 6.89–6.91 (d, 1H), 7.16 (t, 1H), 7.35–7.45 (m, 6H), 7.64–7.68 (m, 4H).

Preparation of Isopropyl [2R (1E, 3R), 3R (4Z), 4R]-7-[tetrahydro-(2-(4-(3-chlorophenoxy)-3-hydroxy-1-butenyl)-4-hydroxy)-3-furanyl]-4-heptenoate (20).

From 23. Tetrabutylammonium fluoride (1 M in THF, 750 mL) was added to a stirred solution of 23 (60.5 g) in THF (250 mL). After 3 h the reaction was quenched with water (2.5 L) and the mixture was extracted with EtOAc (4×2 L). The organic solution was dried (Na$_2$SO$_4$), filtered and concentrated and the product was analyzed by HPLC which showed 20 (90%), the 15-epi-isomer (6%) and Δ$^4$-trans isomer (4%). This material was chromatographed on a Biotage Flash 75-L instrument, eluting with 60% EtOAc-hexane. Product fractions were treated with activated charcoal, filtered through Celite and concentrated in vacuo to give 20 (35 g) as a clear oil. $^1$H NMR (CDCl$_3$): δ 1.21–1.23 (d, 6H), 1.38–1.45 (m, 1H), 1.51–1.58 (m, 1H), 1.73–1.77 (m, 1H), 2.22–2.38 (m, 5H), 2.43–2.50 (m, 2H), 3.85–3.92 (m, 2H), 3.97–3.99 (dd, 1H), 4.06–4.13 (m, 2H), 4.41 (t, 1H), 4.55–4.56 (m, 1H), 4.96–5.00 (m, 1H), 5.32–5.44 (m, 2H), 5.81–5.90 (m, 2H), 6.77–6.82 (d, 1H), 6.91 (s, 1H), 6.93–6.95 (d, 1H), 7.19 (t, 1H).

From 19. Compound 19 (9.4 g, mol) was desilylated as described immediately above to provide 6.5 g of crude 20. Chromatography of this material on silica (70% EtOAc-hexane) provided 6.2 g of semi-pure 20. This material was chromatographed three times on a Biotage Flash 75 (60% EtOAc-hexane), pooling all of the <1% epi and <5% trans fractions. The impure cuts were chromatographed on a Waters DeltaPrep 4000 (1:1 MeOt-Bu-hexane+1.2% EtOH using both a 55–105μ PrepPak column and a 10μ semi-prep column) and the clean cuts were combined with the clean fractions from above and stripped of solvent. Residual solvent was removed in vacuo on a Kugelrohr apparatus to provide 20 (4.5 g) as a clear oil.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A method of selectively reducing enone of formula XIV:

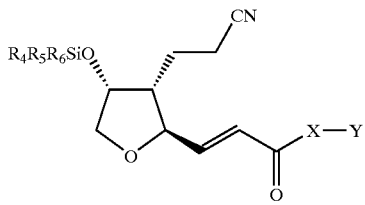

to allylic alcohol of formula XV:

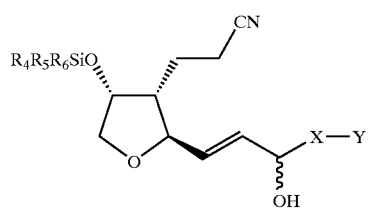

wherein:

$R_4$, $R_5$, $R_6$=same or different=alkyl, cycloalkyl, or aryl;

$X=(CH_2)_q$ or $(CH_2)_qO$; q=1–6; and

Y=a phenyl ring optionally substituted with alkyl, halo, trihalomethyl, alkoxy, acyl, or a free or functionally modified hydroxy or amino group;

or X-Y=$(CH_2)_mY^1$, m=0–6,

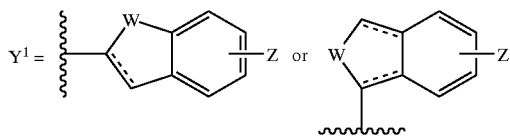

wherein:

W=$CH_2$, O, $S(O)_m$, $NR^{10}$, $CH_2CH_2$, CH=CH, $CH_2O$, $CH_2S(O)_m$, CH=N, or $CH_2NR^{10}$;

m=0–2;

$R^{10}$=H, alkyl, acyl;

Z=H, alkyl, alkoxy, acyl, acyloxy, halo, trihalomethyl, amino. alkylamino, acylamino, OH; and ====is a single or double bond;

comprising, contacting said enone with a reducing agent selected from the group consisting of: (−)-B-chlorodiisopinocampheylborane and (+)-B-chlorodiisopinocampheylborane, in an amount sufficient to effect such reduction.

2. The method of claim 1, wherein the reducing agent is (−)-B-chlorodiisopinocampheylborane.

3. The method of claim 2, wherein the enone is (2R (1E), 3R, 4R)-3-[Tetrahydro-(2-(4-(3-chlorophenoxy)-3-oxo-1-butenyl)-4-(t-butyldiphenylsilyl)oxy)-3-furanyl]propanenitrile, and the resulting alcohol is (2R (1E, 3R), 3R, 4R)-3-[Tetrahydro-(2-(4-(3-chlorophenoxy)-3-hydroxy-1-butenyl)-4-(t-butyldiphenylsilyl)oxy)-3-furanyl]propanenitrile.

4. A process for the preparation of 11-oxa prostaglandin analogs of formula I:

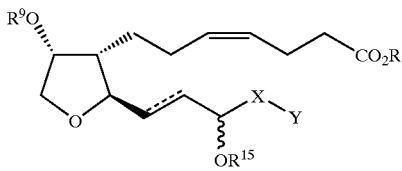

wherein:

R is H or a pharmaceutically acceptable cationic salt moiety, or $CO_2R$ forms a pharmaceutically acceptable ester moiety $R^9O$ and $R^{15}O$ are the same or different and constitute a free or functionally modified hydroxy group;

===is a single or trans double bond;

X=$(CH_2)_q$ or $(CH_2)_qO$; q=1–6; and

Y=a phenyl ring optionally substituted with alkyl, halo, trihalomethyl, alkoxy, acyl, or a free or functionally modified hydroxy or amino group;

or X-Y=$(CH_2)_mY^1$, m=0–6,

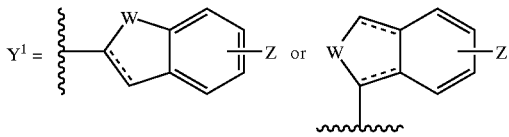

wherein:

W=$CH_2$, O, $S(O)_m$, $NR^{10}$, $CH_2CH_2$, CH=CH, $CH_2O$, $CH_2S(O)_m$, CH=N, or $CH_2NR^{10}$;

m=0–2;

$R^{10}$=H, alkyl, acyl;

Z=H, alkyl, alkoxy, acyl, acyloxy, halo, trihalomethyl, amino, alkylamino, acylamino, OH; and ===is a single or double bond;

comprising:
a) converting 1,4-anhydro-D-glucitol to the corresponding ortho ester;
b) silylating the ortho ester to yield to the corresponding silyl ether;
c) removing the ortho ester group of the silyl ether to yield to the corresponding triol;
d) converting the triol to the corresponding acetonide;
e) oxidizing the free OH group of the acetonide to yield to the corresponding ketone;
f) converting the ketone to the corresponding unsaturated ester;
g) hydrogenating the unsaturated ester to yield the saturated ester;
h) reducing the saturated ester to yield to the corresponding alcohol;
i) converting the alcohol to the corresponding sulfonate;
j) reacting the sulfonate with cyanide to yield to the corresponding nitrile;
k) oxidatively cleaving the acetonide grouping of the nitrile to yield to the corresponding nitrile aldehyde;
l) converting the nitrile aldehyde to the corresponding enone;
m) reducing the enone with a reducing agent selected from (−)-B-chlorodiisopinocampheylborane and (+)-B-chlorodiisopinocampheylborane to yield to the corresponding alcohol;

n) silylating the alcohol to yield to the corresponding bis silyl ether;

o) reducing the bis silyl ether to yield to the corresponding aldehyde;

p) condensing the aldehyde to yield to the corresponding ester; and q) desilylating the ester to yield to the corresponding end product.

5. The method of claim 4, wherein for step (m), the enone is 2R (1E), 3R, 4R)-3[Tetrahydro-(2-(4-(3-chlorophenoxy)-3-oxo-1-butenyl)-4-(t-butyldiphenylsilyl)oxy)-3-furanyl] propanenitrile and the corresponding alcohol is (2R (1E, 3R), 3R, 4R)-3-[Tetrahydro-(2-(4-(3-chlorophenoxy)-3-hydroxy-1-butenyl)-4-(t-butyldiphenylsilyl)oxy)-3-furanyl] propanenitrile.

* * * * *